United States Patent [19]
Chesterfield et al.

[11] Patent Number: 5,662,682
[45] Date of Patent: *Sep. 2, 1997

[54] SPIROID BRAIDED SUTURE

[75] Inventors: Michael P. Chesterfield, Norwalk; Ilya Koyfman, Orange; Matthew E. Hain, New Haven, all of Conn.

[73] Assignee: United States Surgical Corporation, Norwalk, Conn.

[*] Notice: The portion of the term of this patent subsequent to Jan. 26, 2010, has been disclaimed.

[21] Appl. No.: 5,935

[22] Filed: Jan. 15, 1993

Related U.S. Application Data

[63] Continuation of Ser. No. 897,576, Jun. 11, 1992, abandoned, which is a continuation of Ser. No. 651,758, Feb. 7, 1991, abandoned, which is a continuation of Ser. No. 499,173, Mar. 26, 1990, Pat. No. 5,059,213.

[51] Int. Cl.$^6$ .................................................. A61B 17/06
[52] U.S. Cl. ............................................. 606/228; 606/230
[58] Field of Search ................................. 606/224–231; 87/6

[56] References Cited

U.S. PATENT DOCUMENTS

| | | | |
|---|---|---|---|
| 3,187,752 | 6/1965 | Glick | 606/228 |
| 3,565,077 | 2/1971 | Glick | 606/228 |
| 4,014,973 | 3/1977 | Thompson | |
| 4,043,344 | 8/1977 | Landi et al. | |
| 4,047,533 | 9/1977 | Perciaccante et al. | |
| 4,959,069 | 9/1990 | Brennan et al. | 606/228 |
| 5,019,093 | 5/1991 | Kaplan et al. | 606/230 |

OTHER PUBLICATIONS

Brown et al., "Acceleration of Tensile Strength of Incisions Treated with EFG and TGF–beta", Ann. Surg., pp. 788 et seg. (Dec. 19988).

Barbul et al. eds., "Growth Factors and Other Aspects of Wound Healing/Biological and Clinical Implications", *Proceedings of the Second International Symposinm on Tissue Repair*, Tarpon Springs, Florida, May 13–17, 1987 (Alan R. Liss, Inc. New York).

Lynch et al., "Growth Factors in Wound Healing", J. Clin. Invest., vol. 84, Aug. 1989, pp. 640–646.

Brown et al., "Aceleration of Tensile Strength of Ineisions Treated with EFG and TGF–BETA", Ann. Surg p. 78 et seg(12–1988).

Lynch et al., "Growth Factors in wound Healing", J. Clin. Invest., vol. 84 Aug. 1989, pp. 640–646.

*Primary Examiner*—Michael Buiz
*Assistant Examiner*—Gary Jackson

[57] ABSTRACT

A suture is provided with a solid spiroid braid construction. The suture exhibits greater flexibility, better hand and less chatter and drag than tubular braided sutures of known construction.

21 Claims, 4 Drawing Sheets

FIG. 1

MAGNIFICATION - 50X

FIG. 2

MAGNIFICATION = 150X

FIG. 3

MAGNIFICATION = 150X

FIG. 4

MAGNIFICATION = 200X

FIG. 5

MAGNIFICATION = 400X

SPIROID BRAIDED SUTURE

This is a continuation of application Ser. No. 07/897,576 filed on Jun. 11, 1992, now abandoned, which is an FWC of application Ser. No. 07/651,758 filed Feb. 7, 1991, now abandoned which is a continuation of Ser. No. 07/499,173 filed Mar. 26, 1990, now U.S. Pat. No. 5,059,213.

BACKGROUND OF THE INVENTION

This invention relates to a suture possessing a solid spiroid braid.

Sutures intended for the repair of body tissues must meet certain requirements: they must be substantially non-toxic, capable of being readily sterilized, they must have good tensile strength and have acceptable knot-tying and knot-holding characteristics and if the sutures are of the bio-absorbable variety, the bio-absorption of the suture must be closely controlled.

Sutures have been constructed from a wide variety of materials including surgical gut, silk, cotton, polyolefins such as polypropylene, polyamides, polyesters such as polyethylene terephthalate, polyglycolic acid, glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials have been provided as braided structures. Thus, for example, sutures manufactured from silk, polyamide, polyester and bio-absorbable glycolide-lactide copolymer are usually provided as multifilament braids.

Currently available braided suture products are braided on conventional braider-carriers which travel around the perimeter of the braider deck to result in a tubular type braid with the yarns crossing over each other on the surface of the braid. In the larger sizes, e.g., 5/0 and larger, the tubular braid, or sheath, is constructed about a core structure which is fed through the center of the braider. Known tubular braided sutures, including those possessing cores, are disclosed, e.g., in U.S. Pat. Nos. 3,187,752; 3,565,077; 4,014,973; 4,043,344; and, 4,047,533.

Spiroid braided structures per se are known, e.g., rope, sash cord and the like, but heretofore have not been known for use as sutures.

As removed from the package, the currently available tubular braided suture products exhibit one or more deficiencies. Thus, they tend to be stiff and wiry and retain a "set" or "memory" such that at the time of use, it is usually necessary for the surgeon or assistant personnel to flex and stretch the suture to make it more flexible. Furthermore, the surface of these sutures are perceptibly rough. Thus, if one passes one's hand or fingers along the braid, surface irregularities will be readily detected. The result of this rough surface is that the suture will exhibit drag or chatter as it is drawn through tissue, characteristics which militate against smooth, neat, accurately placed wound approximation so necessary to excellence in surgical practice.

SUMMARY OF THE INVENTION

It is an object of this invention to provide a braided suture of improved characteristics, specifically one exhibiting greater flexibility, better hand and less chatter and drag, than braided sutures of known construction.

It is another object of the invention to provide a braided suture exhibiting improved knot security relative to known tubular braided suture constructions.

It is a particular object of the invention to provide a spiroid braided suture exhibiting the foregoing improved characteristics and which, being solid throughout, eliminates the need for a core component and the attendant risk of core popping.

It is yet another object of the invention to apply one or more medico-surgically useful compositions to the spiroid braided suture to enhance or accelerate wound repair and/or tissue growth. A particularly advantageous composition of this type is one containing at least one Human Growth Factor (HGF), preferably in combination with a carrier such as glycerol which protects the HGF from excessive loss of biopotency during storage.

By way of satisfying the foregoing objects as well as other objects of the invention, there is provided in accordance with this invention a suture of solid spiroid braid construction.

Due to the substantially parallel orientation of the fibers relative to its axis, the spiroid braided suture of this invention exhibits improved flexibility and hand and reduced tissue chatter and drag compared with tubular and/or cored braided sutures where the fibers cross over each other.

Unlike tubular braided sutures, the solid spiroid braided suture of this invention shows little if any tendency to kink or snarl. Bends which might cause core popping (the penetration of the core through the braided sheath) in the known types of tubular braided sutures pose no risk of damage to the solid spiroid braided suture of this invention.

Knot security in the spiroid braided suture of this invention is also superior to that obtainable with known tubular braided constructions. Factors contributing to enhanced knot security include the approximately perpendicular orientation of the fibers in the knot relative to the axis of the braid, the reduced density of the knot compared with the knot of a cored suture of equivalent size and the formation of a narrowed down portion which makes the knot more difficult to untie.

The term "suture" as used herein is intended to embrace both the non-absorbable as well as the bio-absorbable varieties.

The expressions "spiroid braid" and "spiroid braided" as applied to the suture of this invention refer to a solid arrangement of discrete units, or bundles, denominated "yarns", made up of individual filaments or fibers with the yarns arranged substantially parallel to the longitudinal axis of the suture and internally engaging each other in a repetitive spiral pattern.

The term "solid" as applied to the suture herein is intended to designate a suture in which the filamentous material of its construction occupies substantially the entire cross-sectional area of the suture with a relatively minor percentage of such area constituting void spaces or interstices between adjacent yarns and fibers. Such a construction contrasts with that of a tubular braided suture which, in the absence of a core component, possesses a lumen which represents a significant percentage of the cross-sectional area of the suture.

DESCRIPTION OF THE PREFERRED EMBODIMENTS

The spiroid braided suture of this invention can be fabricated from a wide variety of natural and synthetic fibrous materials such as any of those heretofore disclosed for the construction of sutures. Such materials include non-absorbable as well as partially and fully bio-absorbable (i.e., resorbable) natural and synthetic fiber-forming polymers. Non-absorbable materials which are suitable for fabricating the spiroid braided suture of this invention include silk, polyamides, polyesters such as polyethylene terephthalate, polyacrylonitrile, polyethylene, polypropylene, silk, cotton, linen, etc. Carbon fibers, steel fibers and other biologically acceptable inorganic fibrous materials can also be employed. Bio-absorbable resins from which the spiroid suture can be fabricated include those derived from glycolic acid, glycolide, lactic acid, lactide, dioxanone, epsilon-caprolactone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077, 3,565,869; 3,620,218; 3,626,948; 3,636,956; 3,736,646; 3,772,420; 3,773,919; 3,792,010; 3,797,499; 3,839,297; 3,867,190; 3,787,284; 3,982,543; 4,047,533; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459–1464 (1979), and D. F. Williams (ed.), *Biocompatibility of Clinical Implant Materials*, Vol. II, ch. 9: "Biodegradable Polymers" (1981).

The defining characteristics of a specific spiroid braided suture in accordance with this invention, apart from the material of its construction, are:

(1) suture size (i.e., suture diameter)

(2) overall suture denier;

(3) the pattern of the interlocking yarns;

(4) pick count;

(5) the number of yarns comprising the braid; and, (6) the denier of the filaments comprising each yarn.

(1) Suture Size (i.e., Suture Diameter)

The suture size can be expressed in terms of standard sizes, corresponding to certain ranges of diameter (in millimeters), as set forth in the United States Pharmacopoeia (USP). Standard sizes of the spiroid braided suture herein are set forth in Table I as follows:

TABLE I

| SUTURE SIZE | |
|---|---|
| USP Suture Size | Diameter (mm) |
| 2 | 0.50–0.599 |
| 1 | 0.40–0.499 |
| 0 (1/0) | 0.35–0.399 |
| 2/0 | 0.30–0.399 |
| 3/0 | 0.20–0.249 |

TABLE I-continued

| SUTURE SIZE | |
|---|---|
| USP Suture Size | Diameter (mm) |
| 4/0 | 0.15–0.199 |
| 5/0 | 0.10–0.149 |
| 6/0 | 0.070–0.099 |
| 7/0 | 0.050–0.069 |
| 8/0 | 0.040–0.049 |

(2) Overall Denier of the Suture

The overall denier of the braided suture can vary from about 50 to about 4000. Within this range, the ranges of overall denier for particular sutures are: from about 50 to about 125 denier; from above about 200 to about 300 denier; from above about 300 to about 500 denier; from above about 500 to about 800 denier; from above about 800 to about 1500 denier; from above about 1500 to about 2000 denier; and, from above about 2000 to about 3600 denier.

(3) Pattern of the Interlocking Yarns

Unlike a tubular braided structure where the yarns form a criss-cross pattern which may be thought of as confined to the surface of a hollow cylinder, the spiroid braided suture of this invention consists of a pattern of interlocking yarns which may be considered as extending from the surface of cylinder to its center thus providing a solid structure as defined above.

Figure 1:
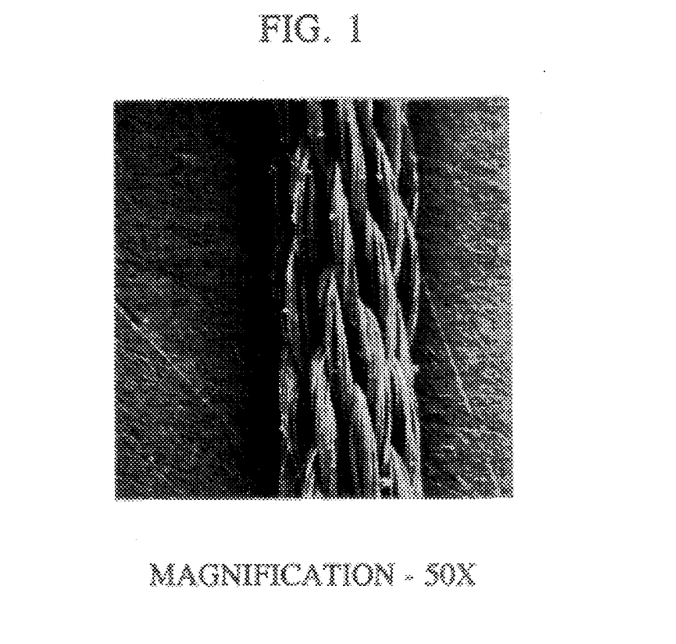
FIGS. 1–5 are photomicrographs of linear (FIGS. 1 and 2) and cross-sectional (FIGS. 3, 4 and 5) views taken by scanning electron microscopy (SEM) of a spiroid braided suture in accordance with the present invention.
Figure 2:
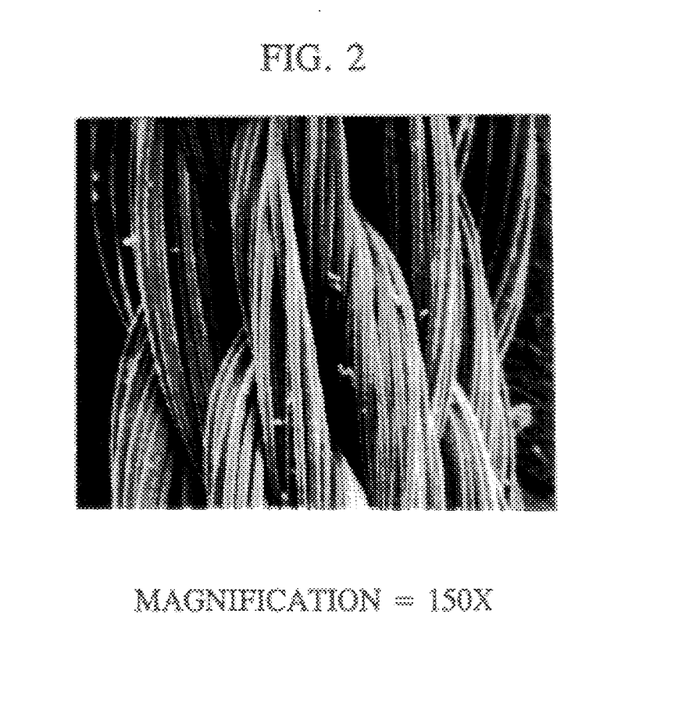
Figure 3:
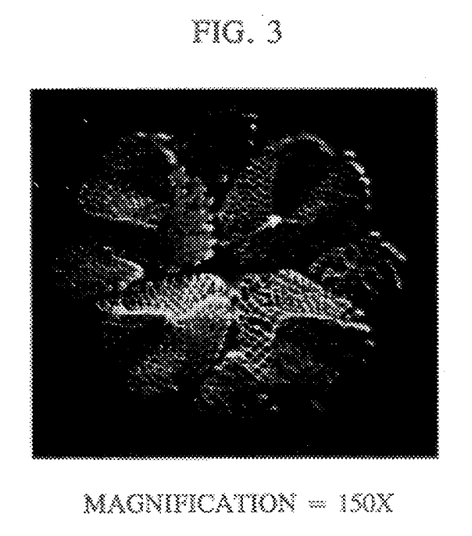
Figure 4:
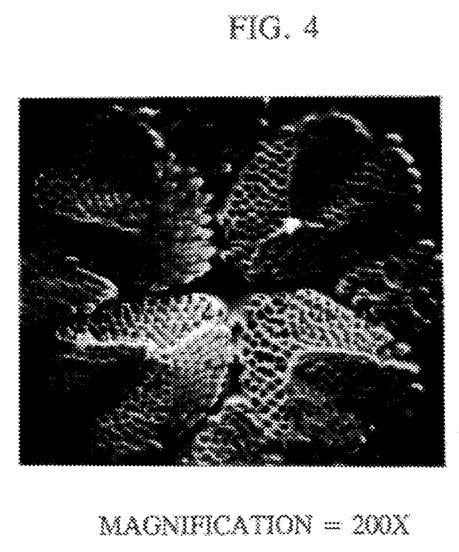
Figure 6:
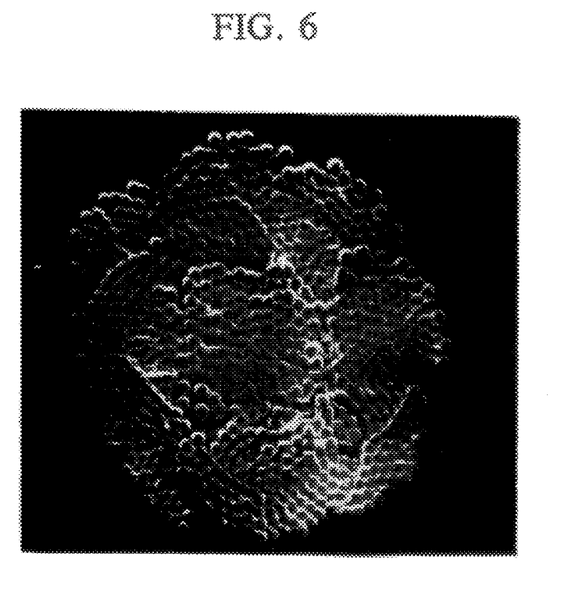
FIGS. 6 and 7 are photomicrographs of cross-sectional (FIG. 6) and linear (FIG. 7) views taken by SEM of a commercially available tubular braided suture possessing a core component; and, FIG. 8 is a graphical representation of the tissue drag of a spiroid braided suture compared with that of two types of commercially available tubular braided sutures.
Figure 7:
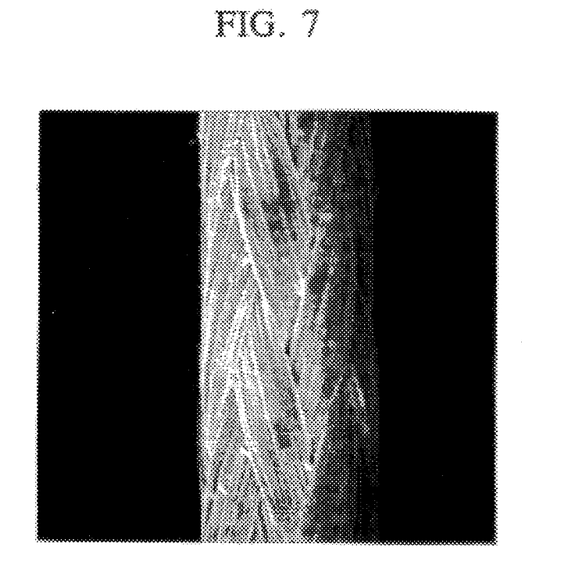
Figure 8:
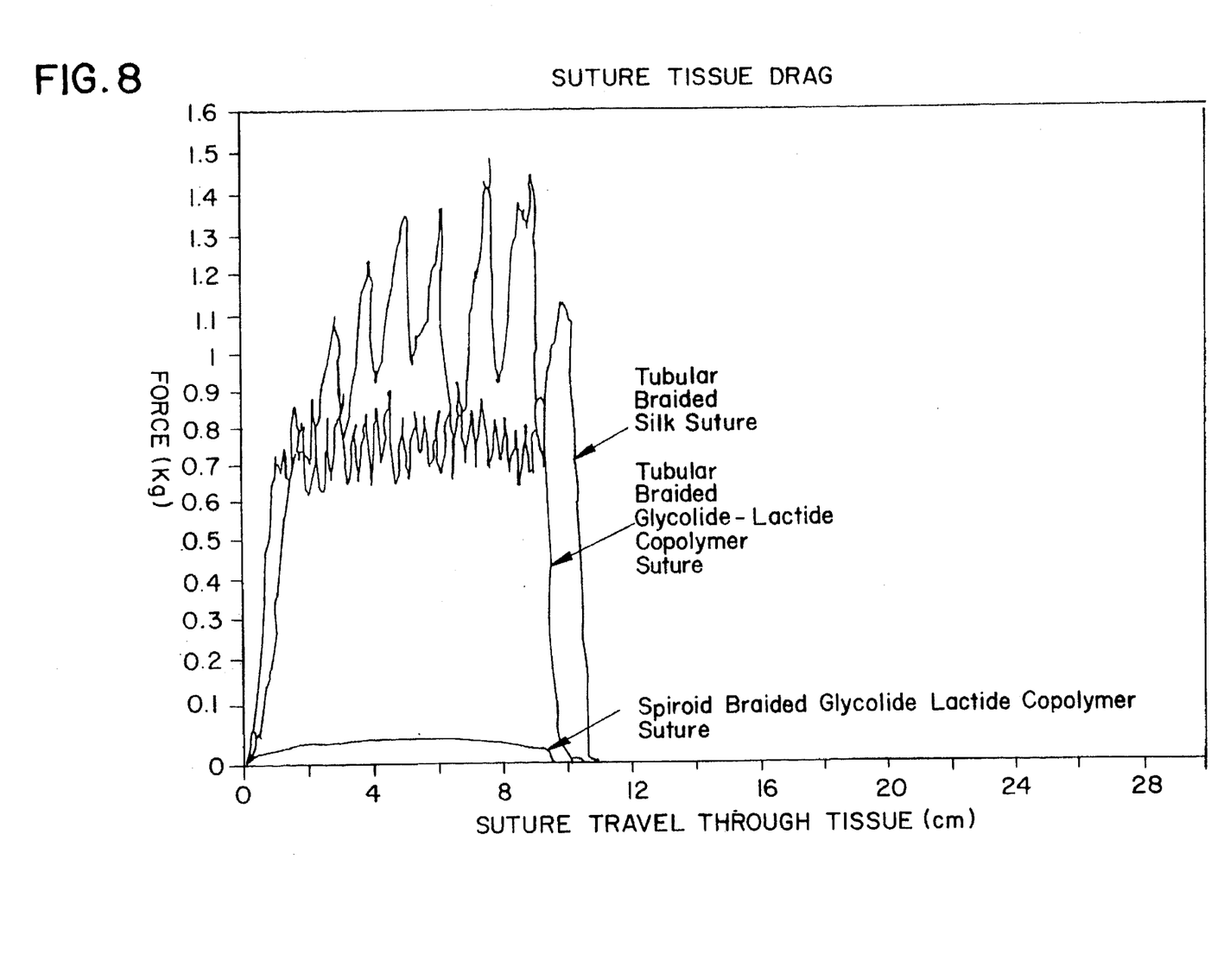

The characteristic pattern of a spiroid braided suture is clearly different from that of a tubular braided suture. In the former, the yarns are essentially parallel to the longitudinal axis of the suture whereas in the latter, the yarns cross over each other at some angle to the longitudinal axis of the suture. The structural differences between a spiroid braided suture of this invention and a tubular braided suture are clearly evident from a comparison of the linear and cross-sectional views of a spiroid braided suture (FIGS. 2 and 3) and a tubular braided suture (FIGS. 6 and 7).

(4) Pick Count

Pick count is the number of stitches per inch lying in a single line parallel to the longitudinal axis of the suture as viewed from the surface of the suture. Suitable pick counts can vary from 40–80 stitches/inch and preferably from 50–70 stitches/inch.

(5) The Number of Yarns

The number of yarns employed in the construction of the suture bears some relation to overall suture denier, the number of yarns generally increasing with the weight of the suture. Thus, across the range of suture weight (denier) indicated above, the spiroid braided suture of this invention can be fabricated with from about 6 up to as many as about 30 individual yarns constructed from individual filaments having the deniers discussed below.

Table II below sets forth broad and preferred ranges for the numbers of yarns which are suitable for the construction of spiroid braided sutures of various ranges of overall denier. The deniers of individual filaments in a yarn can vary from about 0.2 to about 6.0 for the broad range of number of yarns and the deniers of individual filaments can vary from about 0.08 to about 3.0, and advantageously from about 0–0.08 to about 1.4, for the preferred range of number of yarns.

TABLE II

NUMBER OF YARNS RELATED TO SUTURE DENIER

| Overall Suture Denier | Suture Size | Number of Yarns (Broad Range) | Number of Yarns (Preferred Range) |
|---|---|---|---|
| 50 to about 125 | 7/0,8/0 | 6–15 | 6–12 |
| greater than about 125 to about 200 | 6/0 | 6–15 | 6–12 |
| greater than about 200 to about 300 | 5/0 | 6–15 | 6–12 |
| greater than about 300 to about 500 | 4/0 | 6–15 | 9–12 |
| greater than about 500 to about 800 | 3/0 | 9–20 | 12–15 |
| greater than about 800 to about 1200 | 2/0 | 12–25 | 15–20 |
| greater than about 1200 to about 2000 | 0 | 12–25 | 15–20 |
| greater than about 2000 to about 4000 | 1,2 | 15–25 | 20–25 |

While the yarns need not be twisted, it is generally preferred that they be provided with a slight twist so as to minimize snagging during braid construction.

(6) Individual Filament Denier

The individual filaments comprising each yarn can vary in weight from about 0.2 to about 6.0 denier, preferably from about 0.8 to about 3.0 denier and more preferably from about 0.8 to about 1.4 denier. The number of such filaments present in a particular yarn will depend on the overall denier of the suture as well as the number of yarns utilized in the construction of the suture. Table III sets forth some typical numbers of filaments per yarn for both the broad and preferred ranges of filament weight:

TABLE II

NUMBER OF FILAMENTS PER YARN

| approximate minimum | approximate maximum | Filament Denier |
|---|---|---|
| 45 | 1500 | 0.2 |
| 15 | 500 | 0.5 |
| 5 | 200 | 1.5 |
| 3 | 150 | 1.8 |
| 1 | 50 | 6.0 |

It is within the scope of this invention to impregnate the suture with, or otherwise apply thereto, one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (Gentacmycin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the spiroid braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the suture herein, e.g., hEGF (urogastrone), TGF-beta, IGF, PDGD, FGF, etc. These and other useful HGFs and closely related HGF derivatives, methods by which they can be obtained and methods and compositions featuring the use of HGFS to enhance wound healing are variously disclosed inter alia, in U.S. Pat. Nos. 3,883,497, 3,917,824, 3,948,875, 4,338,397, 4,418,691, 4,528,186, 4,621,052, 4,743,679 and 4,717,717; European Patent Applications 0 046 039, 0 128 733, 0 131 868, 0 136 490, 0 147 178, 0 150 572, 0 177 915 and 0 267 015, PCT International Applications WO 83/04030, WO 85/003698, WO 85/01284 and WO 86/02271 and UK Patent Applications GB 2 092 155 A, 2 162 851 A and GB 2 172 890 A, all of which are incorporated by reference herein. Of the known HGFs, hEGF, TGF-beta, IGF, PDGF, FGF are preferred.

In a preferred embodiment of the spiroid braided suture of this invention and in accordance with the disclosure of commonly assigned, copending Hermes et al. U.S. patent application Ser. No. 397,476, filed Aug. 18, 1989, a filling composition comprising a surgical wound healing enhancing amount of at least one HGF and as carrier therefor at least one water soluble, liquid polyhydroxy compound and/ or ester thereof is applied to the suture. The carrier protects the HGF component of the filling composition from excessive degradation or loss of biopotency during storage.

Carriers which are suitable for use in the optional HGF-containing filling composition are substantially water soluble, liquid polyhydroxy compounds and/or their esters. The expression "liquid polyhydroxy compound" contemplates those polyhydroxy compounds which in the essentially pure state are liquids, as opposed to solids, at or about ambient temperature, e.g., from about 15° C. to about 40° C. The preferred polyhydroxy compounds possess up to about 12 carbon atoms and where their esters are concerned, are preferably the monoesters and diesters. Specific HGF carriers which can be used with generally good results are glycerol and its monoesters and diesters derived from low molecular weight carboxylic acids, e.g., monoacetin and diacetin (respectively, glyceryl monoacetate and glyceryl diacetate), ethylene glycol, diethylene glycol, triethylene glycol, 1,2-propanediol, trimethylolethane, trimethylolpropane, pentaerythritol, sorbitol, and the like. Glycerol is especially preferred. Mixtures of the afore-discussed polyhydroxy compounds or esters, e.g., sorbitol dissolved in glycerol, glycerol combined with monoacetin and/or diacetin, etc., are also useful.

When the filling composition is to be applied to spiroid braided suture of the bio-absorbable type, the composition should be essentially water-free since the presence of water is generally deleterious to the long term storage stability of the suture.

When the HGF carrier is of relatively low viscosity (such as may be the case with glycerol), it can be advantageous to incorporate a thickening agent in the filling composition.

Many kinds of pharmaceutically acceptable thickeners can be utilized including water-soluble polysaccharides, e.g., hydroxypropyl methylcellulose (HPMC), and the other materials of this type which are disclosed in European Patent Application 0 267 015 referred to above, polysaccharide gums such as guar, xanthan, and the like, gelatin, collagen, etc., with or without an aqueous vehicle or other solubilizing agent. An especially preferred class of thickeners are the saturated aliphatic hydroxycarboxylic acids of up to 6 carbon atoms and the alkali metal and alkaline earth metal salts and hydrates thereof. Within this preferred class of compounds are those corresponding to the general formula wherein R is hydrogen or methyl, R" is a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinbefore, hydrates of these compounds can also be used. Calcium lactate, especially calcium lactate pentahydrate is a particularly preferred thickener.

Where a thickener is utilized, it will be incorporated in the filling composition in at least that amount required to increase the overall viscosity of the composition to the point where the composition no longer readily drains away from the suture in a relatively short period. In the case of a preferred carrier-thickener combination, namely, glycerol and calcium lactate, the weight ratio of glycerol to calcium lactate can vary from about 1:1 to about 10:1 and preferably is about 7:1.

If desired, the HGF stabilizing component, and if present, optional thickener component, can be dissolved in any suitable solvent or combination of solvents prior to use. To be suitable, the solvent must (1) be miscible with the carrier or carrier-thickener combination at the concentration of these components, (2) have a sufficiently high vapor pressure to be readily removed by evaporation, (3) not appreciably affect the integrity of the surgical device and (4) capable, in combination with the carrier and optional thickener, of wetting the surface of the surgical device. Applying these criteria to a preferred carrier-thickener combination, namely, an admixture of glycerol and calcium lactate, lower alcohols such as methanol and ethanol are entirely suitable solvents.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See, e.g., Tomlinson (Ciba-Geigy Pharmaceuticals, West Sussex, U.K.), "Selective Delivery and Targeting of Therapeutic Proteins", a paper presented at a symposium held Jun. 12-14, 1989 in Boston, Mass., the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of BioGrowth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

The amounts of HGF, carrier and optional component(s) such as thickener, site-specific hybrid protein, carrier protein, etc., identified above which are incorporated in the formulation of the optional filling composition can vary widely and in general will be at least that amount of a particular component which is required to perform its respective function in an effective way. Those skilled in the art employing known or conventional procedures can readily determine optimum amounts of each component for a particular filling composition and particular spiroid braided suture filled therewith.

In general, the HGF(s) can be present in the total filling composition at a level ranging from about 0.1 to about 25,000 micrograms per gram of such composition, preferably from about 0.5 to about 10000 micrograms per gram of composition and most preferably from about 1 to about 500 micrograms per gram of composition.

Application of the HGF-containing filling composition to the spiroid braided suture of this invention can be carried out in any number of ways. Thus, for example, the suture can be submerged in the composition until at least a wound healing enhancing amount of the composition is acquired or otherwise retained by the suture, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart an effective amount of the filling composition to the surgical device.

The foregoing submersion method of filling the suture with HGF-containing filling composition can be conducted continuously or in batch. Thus, a running length of the suture can be continuously passed through a quantity of the filling composition at a velocity which has been previously determined to provide the necessary degree of exposure, or contact time, of the suture with the composition. As the suture emerges from the filling composition, it can be passed through a wiper or similar device to remove excess filling material prior to the packaging operation. In a bach operation, a quantity of suture is merely submerged within the filling composition for the requisite period of time with any excess agent being removed from the suture if desired.

Alternatively, the filling composition and solutions thereof can be applied by spraying, brushing, wiping, etc., on the surfaces of the suture such that the latter will receive and retain at least an effective amount of the composition. Yet another procedure which can be used to apply the filling composition involves inserting the sutures in a package containing an effective amount of the filling composition such that intimate contact between the suture and the composition will be achieved.

In general, amounts of from about 2 to about 25, and preferably from about 5 to about 15 weight percent, of filling composition (exclusive of any solvent) by weight of suture contacted therewith is sufficient to provide significant enhancement of wound healing.

It can also be advantageous to apply one or more coating compositions to the spiroid braided suture of this invention where particular functional properties are desired. Thus, for example, in the case of a bio-absorbable suture which has been treated with a filling composition which includes a storage stabilizing agent such as glycerol for improved long term storage, the storage stabilized article can be coated with a polyethylene oxide-polypropylene oxide block copolymer or polyalkylene glycol, either of which has been further polymerized with glycolide monomer and lactide monomer or glycolide/lactide copolymer to improve surface lubricity and facilitate knot tie-down as disclosed in commonly assigned U.S. patent application Ser. No. 089,733 filed Aug. 26, 1987 and Ser. No. 089,734 filed Aug. 26, 1987, the entire contents of which are incorporated by reference herein.

The following examples are illustrative of the spiroid braided suture of this invention.

EXAMPLES 1–9

These examples illustrate various size spiroid braided sutures, fabricated from non-absorbable as well as from bioabsorbable materials, in accordance with the present invention.

| Example | Suture Size | Overall Suture Denier | Number of Yarns | Denier of Individual Filaments |
|---|---|---|---|---|
| 1 | 7/0 | 50 | 6 | 1.2 |
| 2 | 6/0 | 120 | 9 | 1.2 |
| 3 | 5/0 | 320 | 12 | 1.2 |
| 4 | 4/0 | 430 | 12 | 1.2 |
| 5 | 3/0 | 700 | 15 | 1.2 |
| 6 | 2/0 | 1300 | 20 | 1.2 |
| 7 | 0 (1/0) | 1500 | 20 | 1.2 |
| 8 | 1 | 2250 | 25 | 1.2 |
| 9 | 2 | 2960 | 25 | 1.2 |

The scanning electron photomicrographs of FIGS. 1–5 show a 2/0 spiroid braided suture in accordance with this invention taken at various levels of magnification. The substantially parallel orientation of the individual yarns and fibers relative to the longitudinal axis of the suture is clearly evident from FIGS. 1 and 2 (magnifications of 50× and 150×, respectively). The cross-sectional views of the suture shown in FIGS. 3, 4 and 5 (magnifications of 150, 200 and 400×) show the substantially solid nature of the suture, there being relatively little unfilled space between adjacent yarns.

As a result of their unique construction characteristics, the spiroid braided sutures of this invention exhibit significantly improved flexibility and hand and reduced chatter and drag compared with known sutures.

EXAMPLE 10

This example compares three size 2/0 sutures for tissue drag. Two of the sutures, a tubular braided silk suture and a tubular braided glycolide-lactide copolymer suture, are commercially available. The third, a solid spiroid braided glycolide-lactide copolymer suture, is representative of the suture of this invention.

Figure 5:
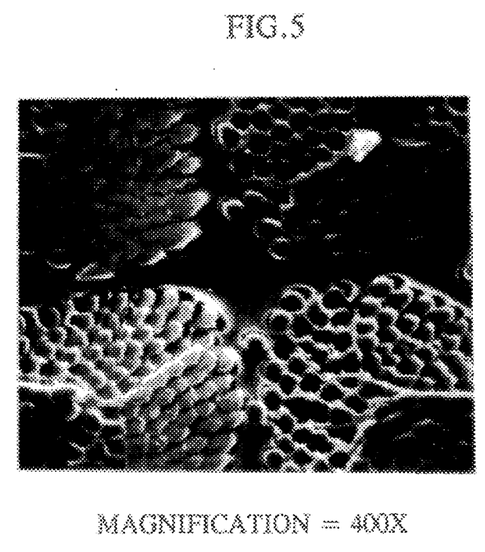

As shown in FIG. 5, the spiroid braided suture exhibited dramatically less tissue drag than either of the two tubular braided sutures.

EXAMPLE 11

This example is illustrative of a size 2/0 spiroid braided glycolide-lactide copolymer suture in accordance with the invention filled with a wound healing enhancing amount of an HGF- and carrier/storage stabilizing agent-containing filling composition.

A solution of glycerol (278 gm), calcium lactate (43 gm) and sterile water (370 gm) was prepared. Human Growth Factor hEGF-51 (152.6 mg) (Creative Biomolecules, Inc., Hopkinton, Mass.) was dissolved volumetrically to 25 mL with the above solution to provide a braided suture filling composition. The composition was placed in the syringe pump of a suture coating apparatus. The syringe pump was set to provide the filling composition at a constant rate and the suture speed was adjusted to apply 17 mL of filling composition to 200 meters of braid. The target concentration of HGF on the braid is 0.52 mg hEGF/meter or approximately 1.8 mg hEFG/gram of braid. After filling, the braid is immediately passed through a 50° drying column. After filling, the spooled braid is removed to a small chamber and stored under a flowing dry nitrogen atmosphere to remove the water from the solution.

What is claimed is:

1. A suture of solid spiroid braid construction.
2. The suture of claim 1 wherein the individual filaments are fabricated from a non-absorbable material.
3. The suture of claim 2 wherein the non-absorbable material is selected from the group consisting of cotton, silk, polyamide and polyolefin.
4. The suture of claim 1 wherein the individual filaments are fabricated from a bio-absorbable polymer.
5. The suture of claim 4 wherein the individual filaments are fabricated from a polymer derived at least in part from a monomer selected from the group consisting of glycolic acid, glycolide, lactic acid and lactide.
6. The suture of claim 1 surface coated with a composition enhancing a functional property of the suture.
7. The suture of claim 1 containing at least one medico-surgically useful substance.
8. The suture of claim 7 wherein the medico-surgically useful substance is a Human Growth Factor.
9. The suture of claim 1 filled with a filling composition comprising a surgical wound healing enhancing amount of at least one Human Growth Factor and as carrier therefor at least one water soluble, liquid polyhydroxy compound and/or ester thereof.
10. The implantable surgical device of claim 9 wherein the polyhydroxy compound is glycerol.
11. The suture of claim 9 wherein the filling composition includes a thickener.
12. The suture of claim 11 wherein the thickener is a saturated aliphatic hydroxycarboxylic acid of the general formula wherein R is a hydrogen or methyl and R' is a metal selected from the group consisting of alkali metal and alkaline earth metal and n is 0 or 1 and hydrates thereof.

13. The suture of claim 12 wherein the thickener is calcium lactate.
14. The suture of claim 9 wherein the carrier is glycerol and the thickener is calcium lactate.
15. The suture of claim 1 treated with a storage stabilizing agent.
16. The suture of claim 15 wherein the storage stabilizing agent is glycerol.

17. The suture of claim 1 wherein the number of yarns is at least 6.

18. The suture of claim 1 wherein the number of yarns is at least 9.

19. The suture of claim 1 wherein the number of yarns is at least 12.

20. The suture of claim 1 wherein the number of yarns is at least 15.

21. The suture of claim 1 wherein the number of yarns is at least 24.

* * * * *